(12) United States Patent
Mattner et al.

(10) Patent No.: US 7,935,348 B2
(45) Date of Patent: May 3, 2011

(54) COMBINATION THERAPY FOR THE TREATMENT OF ALZHEIMER'S DISEASE

(75) Inventors: Frank Mattner, Vienna (AT); Walter Schmidt, Vienna (AT)

(73) Assignee: Affiris Forschungs-und Entwicklungs GmbH, Vienna (AT)

( * ) Notice: Subject to any disclaimer, the term of this patent is extended or adjusted under 35 U.S.C. 154(b) by 955 days.

(21) Appl. No.: 11/571,970

(22) PCT Filed: Jul. 6, 2005

(86) PCT No.: PCT/EP2005/053224
§ 371 (c)(1),
(2), (4) Date: Jan. 11, 2007

(87) PCT Pub. No.: WO2006/005706
PCT Pub. Date: Jan. 19, 2006

(65) Prior Publication Data
US 2008/0051690 A1   Feb. 28, 2008

(30) Foreign Application Priority Data

Jul. 13, 2004   (AT) ................ A 1185/2004

(51) Int. Cl.
| A61K 39/00 | (2006.01) |
| A61K 38/08 | (2006.01) |
| A61K 38/10 | (2006.01) |
| A61K 47/48 | (2006.01) |
| A61M 1/34 | (2006.01) |
| A61M 1/20 | (2006.01) |

(52) U.S. Cl. ............... 424/185.1; 424/140.1; 424/278.1; 604/6.01

(58) Field of Classification Search ................ None
See application file for complete search history.

(56) References Cited

U.S. PATENT DOCUMENTS

| 6,551,266 | B1 | 4/2003 | Davis, Jr. |
| 2007/0026029 | A1 | 2/2007 | Mattner et al. |

FOREIGN PATENT DOCUMENTS

| WO | 00 72880 | 12/2000 |
| WO | 03 000719 | 1/2003 |
| WO | 03 051374 | 6/2003 |
| WO | 2004 013172 | 2/2004 |
| WO | 2004 056318 | 7/2004 |
| WO | 2004 062556 | 7/2004 |
| WO | 2005 025651 | 3/2005 |
| WO | 2006 005707 | 1/2006 |

OTHER PUBLICATIONS

Janus C et al. A beta peptide immunization reduces behavioral impairment and plaques in a model of Alzheimer's disease. Nature, 2000; 408:979-982.*
Morgan D et al. A beta peptide vaccination prevents memory loss in an animal model of Alzheimer's disease. Nature, 2000; 408:982-985.*
Perrin RJ et al. Multimodal techniques for diagnosis and prognosis of Alzheimer's disease. Nature, Oct. 2009; 461(7266):916-922.*
Solomon B. Immunological approaches as therapy for Alzheimer's disease. Expert Opin. Biol. Ther. 2002; 2(8):907-917.*
Vickers JC. A vaccine against Alzheimer's disease: developments to date. Drugs Aging. 2002; 19(7):487-494.*
J. McLaurin, et al., "Therapeutically Effective Antibodies Against Amyloid-Beta Peptide Target Amyloid-Beta Residues 4-10 and Inhibit Cytotoxicity and Fibrillogenesis" Nature Medicine, vol. 8, No. 11, XP 002288573, pp. 1263-1269, 2002.
Frank L. Heppner, et al., "Current Concepts and Future Prospects for Alzheimer Disease Vaccines", Alzheimer Disease and Associated Disorders, vol. 18, No. 1, XP 008057356, pp. 38-43, 2004.
Ulrich Reineke, et al., "Identification of Distinct Antibody Epitopes and Mimotopes From a Peptide Array of 5520 Randomly Generated Sequences", Journal of Immunological Methods, vol. 267, No. 1, XP 004372978, pp. 37-51, 2002.
Frederique Bard, et al., "Peripherally Administered Antibodies Against Amyloid Beta-Peptide Enter the Central Nervous System and Reduce Pathology in a Mouse Model of Alzheimer Disease", Nature Medicine, vol. 6, No. 8, pp. 916-919, 2000.
Dale Schenk, et al., "Immunization With Amyloid-Beta Attenuates Alzheimer-Disease-Like Pathology in the PDAPP Mouse", Letters to Nature, vol. 400, pp. 173-177, 1999.
Christoph Hock, et al., "Generation of Antibodies Specific for Beta-Amyloid by Vaccination of Patients With Alzheimer Disease", Nature Medicine, vol. 8, No. 11, pp. 1270-1275, 2002.
U.S. Appl. No. 12/752,451, filed Apr. 1, 2010, Mattner.

* cited by examiner

*Primary Examiner* — Elizabeth C. Kemmerer
*Assistant Examiner* — Kimberly A. Ballard
(74) *Attorney, Agent, or Firm* — Oblon, Spivak, McClelland, Maier & Neustadt, L.L.P.

(57) ABSTRACT

The invention relates to a method for treating Alzheimer's disease by inducing sequestration of amyloid β into a plasma with a Aβ-mimotope peptide, and treatment with an apheresis device such that a fixed carrier can come into contact with the blood or plasma flow and includes a receptor that binds to an amyloid-β precursor-protein (APP), the APP being removed from the blood with the apheresis device.

10 Claims, No Drawings

COMBINATION THERAPY FOR THE TREATMENT OF ALZHEIMER'S DISEASE

CROSS-REFERENCE TO RELATED APPLICATIONS

This application is a 371 of PCT/EP05/53224 filed Jul. 6, 2005 and claims the benefit Austrian application 1185/2004 filed Jul. 13, 2004.

The invention relates to a combination therapy for the prevention or treatment of the Alzheimer's Disease as well as a kit for implementing said combination therapy.

Amyloid-β peptide (Aβ) plays a central role in the neuropathology of Alzheimer's disease (AD) (Roher et al 1993: "β-Amyloid-(1-42) is a major component of cerebrovascular amyloid deposits: Implications for the pathology of Alzheimer disease" PNAS 90:10836) Familial forms of the disease have been linked to mutations in the amyloid precursor protein (APP) and the presenilin genes. Disease-linked mutations in these genes result in increased production of the 42-amino acid form of the peptide (Aβ42), which is the predominant form found in the amyloid plaques of Alzheimer's disease. An animal model for the disease is commercially available. The PDAPP transgenic mouse, which overexpresses mutant human APP (in which the amino acid at position 717 is F instead of V) progressively develops many of the neuropathological hallmarks of Alzheimer's disease in an age- and brain-dependent manner (Games et al 1995: "Alzheimer-type neuropathology in transgenic mice overexpressing V717F β-amyloid precursor protein" Nature 373: 523).

Vaccination studies with a "normal", not mimotope-based vaccine have already been performed. Transgenic animals were immunized with aggregated Aβ42, either before the onset of AD-type neuropathologies (6 weeks) or at an older age (11 months): Immunization of young animals prevented the development of plaque formation, neuritic dystrophy and astrogliosis. Treatment of older animals markedly reduced AD-like neuropathologies. This experimental vaccination approach induced the development of antibodies against Aβ42 able to cross the blood-brain barrier and attack amyloid plaques (Schenk et al 1999: "Immunization with amyloid-β attenuates Alzheimer-disease-like pathology in the PDAPP mouse" Nature 400:173). The plaques are subsequently removed by several mechanisms, including Fc-receptor mediated phagocytosis (Bard et al 2000: "Peripherally administered antibodies against amyloid β-peptide enter the central nervous system and reduce pathology in a mouse model of Alzheimer's disease" Nature Med 6:916). This vaccine was also able to delay memory deficits (Janus et al 2000 "Aβ peptide immunization reduces behavioural impairment and plaques in a model of Alzheimer's disease" Nature 408: 979).

A highly promising immunization therapy for AD has been in clinical trials since late 1999. Immunization is presumed to trigger the immune system to attack the plaques and clear these deposits from the affected human brain, although the precise mechanism underlying needs to be characterized in more detail.

These clinical trials were conducted by the pharmaceutical company Elan in conjunction with its corporate partner, American Home Products (therapeutic vaccine AN-1792, QS21 as adjuvant). Phase I trials were successfully completed in 2000. Phase II trials were begun late 2001 to test efficacy in a panel of patients with mild to moderate AD.

Now these phase II trials have been permanently discontinued due to neuroinflammation in several patients (Editorial 2002 "Insoluble problem?" Nature Med 8:191). The symptoms included aseptic meningoencephalitis leading to the immediate halt of these world-wide trials. In the worst case scenario, affected patients will be shown to have mounted an autoimmune response—a risk inherent in many immunotherapies. Autoimmune complications could have been anticipated given the ubiquity of APP, which of course bears antigenic determinants in common with its proteolytic product. More recently, additional studies concentrated on the nature of aggregated Aβ42 immunization-induced antibodies (in humans and mice) revealing that most antibodies recognize a small domain between amino acid 4 and 10 of Aβ42 (Aβ4-10). The mouse antibodies were able to block Aβ fibrillogenesis and disrupted pre-existing Aβ fibers (McLaurin et al 2002: "Therapeutically effective antibodies against amyloid-β peptide target amyloid-β residues 4-10 and inhibit cytotoxicity and fibrillogenesis" Nature Med 8:1263). Of note, the human antibodies do not react with APP exposed on the surface of cells or any other non-aggregated proteolytic product of the precursor (Hock et al 2002: "Generation of antibodies specific for β-amyloid by vaccination of patients with Alzheimer disease" Nature Med 8:1270). A clear difference was observed between human and mouse sera: In contrast to human antibodies, mouse antibodies detect monomeric, oligomeric, and fibrillar Aβ. This is of importance and may be a prerequisite for the therapeutic potency since evidence is accumulating that small oligomers of Aβ, which are not recognized by human anti-Aβ, are the major toxic players in the disease (Walsh et al 2002: "Naturally secreted oligomers of amyloid β protein potently inhibit hippocampal long-term potentiation in vivo" Nature 416:535). Thus, a potential new strategy is the immunization with a vaccine containing β-amyloid amino acids 4-10 (instead of aggregated Aβ42). Despite unknown efficacy this strategy may also face autoimmune problems since patients shall be directly immunized with a (linear B cell) "self" epitope.

Despite these disappointing developments in recent AD vaccination strategies, an Aβ vaccine is still regarded as the most promising way for combatting AD. However, there is an urgent need for improvements and new strategies in AD vaccination. Especially, such a vaccine should not induce autoreactive T and/or B cells.

Nevertheless, also more and more other therapeutics are being developed which should prevent amyloid-β production, amyloid-β-aggregation or neurotoxic events triggered by said aggregates. The therapeutic strategies with respect to AD which have so far been explored are summarized in the survey article of Wolfe (Nature Reviews Drug Discovery 1 (2002) 859-866).

The basis for the formation of amyloid-β plaques is the so-called amyloid-β precursor protein (APP) which is an integral transmembrane protein (for which no known physiological function has been clearly proven either; however, most recent research results suggest that APP acts as so-called membrane cargo receptor for kinesin I). APP is proteolytically cleaved by so-called secretases, wherein in particular an Aβ peptide of 40 amino acids in length (Aβ40) is physiologically formed. Other, shorter and longer forms of Aβ also develop, especially a 42-amino-acid version (Aβ42) having high aggregation potential. Consequently said Aβ42 form is the form which occurs most in amyloid plaques. This is why one possible treatment strategy for AD is mainly focussed on attacking secretases which are responsible for said different cleavages (α- and especially β- and γ-secretase). Thus, it has been tried to use modulators and inhibitors, respectively, for said enzymes in AD treatment (such as, e.g., benzodiazepines, sulphonamides, benzocaprolactames).

A further gene which is associated with AD is apolipoprotein E, wherein therefor three allele variants exist (APOE2, APOE3 and APOE4) It has been shown that persons with one or two copies of APOE4 run a greater risk of getting AD than carriers of APOE2 compared with the total population. It has also been shown that persons taking statins, i.e. medicaments inhibiting cholesterol biosynthesis, run a significantly reduced risk of getting AD. This is why a further treatment strategy for AD focuses one inhibiting cholesterol biosynthesis, e.g. with statins.

A further aspect in treating AD is the inhibition of amyloid aggregation in cerebral plaques which could, i.e., be realized by secretase inhibitors as well. It has further been suggested to reduce the zinc content, since zinc, if present in physiologically relevant concentrations, can induce the aggregation of Aβ.

Further treatment strategies for AD which have been proposed in the prior art concern the prevention of APP expression and the increase in Aβ clearance, wherein for said prevention substances were searched for which interact with the APP promoter region. With respect to Aβ clearance, an increase in the activity of certain proteases, such as the insulin-degrading enzyme and neprolysin, or the peripheral application of anti-Aβ antibodies was suggested (De Mattos et al., PNAS 98 (15) (2001), 8850-8855). Such tests, however, already led to contradicting results in the mouse model (Wolfe, (2002). Finally, it was attempted to redissolve already existing amyloid plaques, e.g. by reducing the amyloid-β level in the serum of AD patients. In this context it was also proposed to reduce plague deposits of β-amyloid proteins in the brain by employing apheresis methods (U.S. Pat. No. 6,551,266, wherein it is proposed to remove macromolecules with a molecular weight of more than 500 kD by apheresis), yet without demonstrating it in AD. Nevertheless, dissolution of already existing plaques in brain cells is not directly possible by apheresis methods (plaques or molecules with >500 kd cannot cross the blood/brain barrier).

As mentioned, the presence of β-amyloid (Aβ40 and Aβ42) plaques is the most striking pathological feature of AD. This is why the reduction of Aβ is regarded as the primary pharmaceutical aim in AD prophylaxis and therapy. Despite the described amyloid removal induction of anti-Aβ antibodies by means of active immunization, clinical tests have so far failed in said immunization due to severe side effects which has led to a stop of the treatment. More recent preclinical results showed that antibodies may (also) lead to the peripheral reduction of Aβ and may thus possibly change the Aβ periphery brain dynamics.

It has further been shown that a peripheral treatment with an agent which has a high affinity to Aβ (such as, e.g. gelsolin or GM1) leads to a reduction of the Aβ amount in the brain (Masouka et al., Journal of Neuroscience 2003: 29-33). Accordingly, compounds have been proposed as a general approach which can reduce the Aβ content in the plasma and reduce or prevent amyloidose in the brain. Based thereon, new therapeutic agents could be developed, the activity of which does not depend on crossing the blood/brain barrier.

A method-depending effect on the Aβ content in the plasma has been shown for said plasma-Aβ-sequestration-induced Aβ efflux from the brain: the Aβ content in the plasma was not reduced by gelsolin; instead, administration of gelsolin and passive immunization with anti-Aβ monoclonal antibodies led to an increased Aβ content in the plasma. The Aβ load in the brain, however, was reduced only when using relatively young APP transgenic mice in the experiment; when using mice older than 6 months, the treatment turned out to ineffective. This could be ascribed to the increased insolubility of Aβ in the brain of older mice. On the other hands a longer term of treatment could possibly be successful, yet neither the administration of gelsolin or GM1, nor the passive immunization are suitable for long-term administration.

It is therefore the aim of the present invention to provide a new treatment and prevention strategy for Alzheimer's Disease, in particular a strategy which is also based on a successful immunization.

Accordingly, the present invention provides a combination therapy comprising an Aβ-efflux-inducing agent and an Aβ-peptide-specific apheresis. According to the invention, the Aβ efflux is induced (by agents, such as, e.g., gelsolin, GM1, an Aβ-specific active or passive vaccine) and said efflux is sustained by an Aβ apheresis. In this context, even an active immunization effected once or twice with a vaccine, which contains Aβ, Aβ derivatives or Aβ mimotopes, is sufficient to induce a IgM and/or IgG-mediated sequestration of plasma Aβ.

This is why an aspect of the invention which is of particular priority concerns a kit for preventing or treating Alzheimer's Disease (AD), comprising an agent for inducing a sequestration of amyloid β (Aβ) in plasma, and an apheresis device comprising a solid carrier which can be brought into contact with the blood or with the plasma flux, and having a receptor that binds the amyloid-β-precursor protein (APP).

In the inventive kit the APP-binding receptor is preferably selected from anti-APP antibodies, (soluble) Aβ-binding receptors, such as, e.g. anti-Aβ40 antibodies or anti-Aβ42 antibodies, APP-binding proteins, in particular gelsolin, apoJ or apoE, APP-binding peptides, APP-binding gangliosides, in particular GM1, or APP-binding nucleic acids, in particular aptamers, or mixtures of said receptors.

In the kit, a sterile and pyrogen-free column is preferably used as apheresis carrier.

In the kit, the agent for inducing a sequestration of amyloid β (Aβ) in plasma is preferably select from agents having a high affinity to Aβ in particular gelsolin or GM1, an Aβ-specific peptide ligand or nucleic acid ligand, an Aβ-specific active or passive vaccine or Aβ-specific humanized monoclonal antibodies.

The Aβ-specific active vaccine preferably X is an Aβ derivative or an Aβ mimotope.

Particularly preferred Aβ derivatives are selected from peptides which partly or entirely consist of D-amino acids and/or which do not consist of natural amino acids.

Aβ mimotopes preferably consist of or comprise a peptide of formula

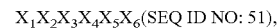

$X_1X_2X_3X_4X_5X_6$(SEQ ID NO: 51), wherein $X_1$ is an amino acid, except C,
$X_2$ is an amino acid, except C,
$X_3$ is an amino acid, except C,
$X_4$ is an amino acid, except C,
$X_5$ is an amino acid, except C,
$X_6$ is an amino acid, except C,
and wherein $X_1X_2X_3X_4X_5X_6$ (SEQ ID NO: 51) is not DAEFRH (SEQ ID NO: 1), said peptide having a binding capacity to an antibody being specific for the natural N-terminal Aβ42 sequence DAEFRH (SEQ ID NO: 1), and 5-mers thereof having a binding capacity to said antibody being specific for the natural N-terminal Aβ42 sequence DAEFRH (SEQ ID NO: 1).

In particularly preferred peptides of formula X1X2X3X4X5X6 (SEQ ID NO: 51),

X1 is G or an amino acid with a hydroxyl group or a negatively charged amino acid, preferably E, Y, S or D,
X2 is a hydrophobic amino acid or a positively charged amino acid, preferably I, L, V, K, W, R, Y, F or A,
X3 is a negatively charged amino acid, preferably D or E,
X4 is an aromatic amino acid or L, preferably Y, F or L,
X5 is H, K, Y, F or R, preferably H, F or R, and
X6 is S, T, N, Q, D, E, R, I, K, Y or G, preferably T, N, D, R, I or G.

In this context, the 20 amino acids which naturally occur in proteins can be replaced by chemical analogues or by D-amino acids; e.g. L, I and V can be replaced by Nle, Nva, Cha or alpha amino acids with other linear or cyclic aliphatic side chains, W and F by aromatic amino acids and R and K by alkaline amino acids, such as, e.g. ornithine or homoarginine. Serine and threonine are suitable for the substitution by amino acids with aliphatic and/or aromatic side chains with terminal OH group. Efficiency and effectiveness of such an exchange can be checked easily with the experimental model which is described, e.g. in PCT/EP04/00162. Additionally, steric considerations can also be taken into account (by the aid of computer models with respect to the binding of the antibody to the peptide.

Particularly suitable epitopes are selected from at least one of the following epitopes: EIDYHR (SEQ ID NO: 2), ELDYHR (SEQ ID NO: 3), EVDYHR (SEQ ID NO: 4), DIDYHR (SEQ ID NO: 5), DLDYHR (SEQ ID NO: 6), DVDYHR (SEQ ID NO: 7), DIDYRR (SEQ ID NO: 8), DLDYRR (SEQ ID NO: 9), DVDYRR (SEQ ID NO: 10), DKELRI (SEQ ID NO: 11), DWELRI (SEQ ID NO: 12), YREFFI (SEQ ID NO: 13), YREFRI (SEQ ID NO: 14), YAEFRG (SEQ ID NO: 15), EAEFRG (SEQ ID NO: 16), DYEFRG (SEQ ID NO: 17), ELEFRG (SEQ ID NO: 18), DRELRI (SEQ ID NO: 19), DKELKI (SEQ ID NO: 20), DRELKI (SEQ ID NO: 21), GREFRN (SEQ ID NO: 22), EYEFRG (SEQ ID NO: 23), DWEFRDA (SEQ ID NO: 24), SWEFRT (SEQ ID NO: 25), DKELR (SEQ ID NO: 26), SFEFRG (SEQ ID NO: 27), DAEFRWP (SEQ ID NO: 28), DNEFRSP (SEQ ID NO: 29), GSEFRDY (SEQ ID NO: 30), GAEFRFT (SEQ ID NO: 31), SAEFRTQ (SEQ ID NO: 32), SAEFRAT (SEQ ID NO: 33), SWEFRNP (SEQ ID NO: 34), SWEFRLY (SEQ ID NO: 35), SWELRQA (SEQ ID NO: 36), SVEFRYH (SEQ ID NO: 37), SYEFRHH (SEQ ID NO: 38), SQEFRTP (SEQ ID NO: 39), SSEFRVS (SEQ ID NO: 40), DWEFRD (SEQ ID NO: 41), DAELRY (SEQ ID NO: 42), DWELRQ (SEQ ID NO: 43), SLEFRF (SEQ ID NO: 44), GPEFRW (SEQ ID NO: 45), GKEFRT (SEQ ID NO: 46), AYEFRH (SEQ ID NO: 47), DKE(Nle)R (SEQ ID NO: 48), DKE(Nva)R (SEQ ID NO: 49), DKE(Cha)R (SEQ ID NO: 50).

According to the invention an Aβ42 mimotope is used for vaccination against AD: The mimotope induces the production of antibodies against Aβ42 but not against the native APP. The mimotope may be identified with a (monoclonal) antibody and (commercially available) peptide libraries (e.g. according to Reineke et al. 2002: "Identification of distinct antibody epitopes and mimotopes from a peptide array of 5520 randomly generated sequences" J Immunol Methods 267:37). A (monoclonal) antibody is used that does not recognize APP but detects only different Aβ species with amino-terminal aspartic acid (an example of such an antibody is described in Johnson-Wood et al 1997: "Amyloid precursor protein processing and Aβ42 deposition in a transgenic mouse model of Alzheimer disease" PNAS 94:1550). Such an antibody has been proven to be an ideal tool to identify vaccine-suitable mimotopes in the course of the present invention. Although such monoclonal anti-bodies were shown to have beneficial effects in a mouse model of AD when directly administered to mice (Bard et al 2000: "Peripherally administered antibodies against amyloid β-peptide enter the central nervous system and reduce pathology in a mouse model of Alzheimer disease" Nature Med 6:916), these antibodies have never been proposed to be used as mimotope search tools for isolating AD vaccine compounds.

In the prior art, all efforts were concentrated on the naturally occurring Aβ peptide. As mentioned above, Aβ peptide vaccine clinical trials were stopped due to neuroinflammatory events. Indeed, T cell epitope prediction programs (BIMAS for MHC class I-restricted epitopes and TEPITOPE for MHC class II-restricted epitopes) propose high score (self) epitopes within the sequence. This could imply that the neuroinflammatory events are due to autoimmune reactions which would make such a vaccine unsuitable for a general application.

In contrast to such Aβ vaccines proposed by the prior arts no autoimmune reactions are expected to occur during treatment with a vaccine containing a mimotope according to the present invention, because the (monoclonal) antibody used for mimotope identification according to the present invention does not recognize APP and the mimotope sequence is different from Aβ42-derived self sequences that have been used in trials so far or shall be used in future trials.

The antibody used for the mimotope identification according to the present invention detects the Aβ-derived amino acid sequence DAEFRH (SEQ ID NO:1) (=original epitope) with a free amino terminal aspartic acid, thus it does not recognize native APP. The antibody may be a monoclonal or polyclonal antibody preparation or any antibody part or derivative thereof, the only prerequisite is that the antibody molecule specifically recognizes the DAEFRH (SEQ ID NO:1) epitope, i.e. that it does not bind to the natural N-terminally prolonged forms of the amyloid precursor protein, which means that the binding capacity to the DAEFRH (SEQ ID NO:1) epitope is at least 100 times, preferably at least 1000 times, more preferred at least $10^5$ times, higher than to the APP molecule. The antibody may be an antibody showing the same or a higher birding capacity to the DAEFRH (SEQ ID NO:1) sequence as the antibody described by Johnson-Wood et al., 1997. Of course, also antibodies with a lower binding capacity may be used (>10%, >50% or >80% of the binding capacity of the Johnson-Wood et al. antibody), although the higher binding capacity is more preferred.

The compounds according to the invention bind to those antibodies with comparable specificity as the DAEFRH (SEQ ID NO:1) sequence.

The mimotope to be used according to the invention has a preferred length of 5 to 15 amino acids. Said compound may be present in the vaccine in an isolated (peptide) form or may be coupled to other molecules or may be complexed, such as pharmaceutical carrier substances or polypeptide, lipid or carbohydrate structures. The mimotopes according to the invention preferably have a (minimum) length of between 5 and 15, 6 and 12 amino acid residues specifically between 9 and 11. The mimotopes can, however, be (covalently or non-covalently) coupled to unspecific linkers or carriers, in particular peptide linkers or protein carriers. Furthermore, the peptide linkers or protein carriers may consist of T cell helper epitopes or contain the same.

The pharmaceutically acceptable carrier preferably is KLH, tetanustoxoid, albumin-binding protein, bovine serum albumin, a dendrimer (MAP; Biol. Chem. 358: 581) as well as the adjuvant substances described in Singh et al. Nat. Biotech 17 (1999; 1075-1081 (in particular those indicated in table 1 of said document) and in O'Hagan et al. Nature review, Drug Discovery 2 (9) (2003) 727-735 (in particular the endogenous immuno-potentiating compounds and dispensing systems described therein) or mixtures thereof. Moreover, the vaccine composition may contain aluminum hydroxide.

A vaccine which comprises the present compound (mimotope) and the pharmaceutically acceptable carrier can be administered in any suitable way of application, e.g. i.v., i.p., i.p., intranasally, orally, subcutaneously, etc., and in any suitable dispensing device (O'Hagan et al., Nature Reviews, Drug Discovery 2 (9), (2003), 727-735). The vaccine typically contains the inventive compound in an amount of between 0.1 ng and 10 mg, preferably 10 ng and 1 mg, in particular 100 ng and 100 µg or, alternatively, e.g. between 100 fMol and 10 µMol, preferably 10 pMol and 1 µMol, in particular 100 pMol and 100 nMol. The vaccine may also contain typical adjuvants, e.g. buffers, stabilizers, etc.

According to the present invention, an apheresis device is provided for maintaining the Aβ efflux after initiation in the course of the combination therapy, said device comprising a solid carrier which can be brought into contact with the blood or plasma flux, said carrier comprising an amyloid-β-precursor-protein (APP)-binding receptor. With the present apheresis device AD patients and persons running the risk of getting AD may be specifically cleared from APP or APP decomposition products, in particular Aβ40 or Aβ42, by means of apheresis and, thus, the effect of Aβ sequestration can be maintained in the first step. It is known that there is a dynamic equilibrium of Aβ42 between the central nervous system (CNS) and the plasma. As mentioned above, it could be shown in the mouse model (DeMattos PNAS 2001, see above) that peripheral application of anti-Aβ antibodies influences the CNS and plasma Aβ42 clearance and reduces the Aβ42 load in the brain, without anti-Aβ antibodies crossing the blood/brain barrier. Matsuoka et al. (Journal of Neuroscience 2003: 29-33) confirmed said results by peripherally applying other Aβ42-binding molecules (gelsolin and GM1). With this the process of plaque development can be prevented at a very good accessible site in the brain, namely already in the blood, i.e. then said proteins and decomposition peptides, respectively, cannot return to the brain any longer and cannot aggregate there. The process of plaque development in the brain can also be prevented by capturing Aβ42 in the blood. In doing so, it is not critical whether the receptors in the apheresis device, which are brought into contact with the blood or plasma of the patient, are specific for Aβ42 or other decomposition forms of APP, the only essential thing is that APP and its (proteolytic) decomposition products, in particular Aβ42, are eliminated from the blood by said specific adsorption, so that no "wrong" protein decomposition (namely to Aβ42) occurs or no plaques develop. Consequently, the present invention is based on a completely different application approach for apheresis as compared to U.S. Pat. No. 6,551, 266, namely on eliminating already potential structural plaque elements and not the plaques themselves. Besides, elimination of plaques by apheresis can be excluded a priori as not being effective for treating AD by apheresis, since the blood apheresis cannot reach the regions in the brain where plaques develop.

On the other hand, compared to other methods which lead to depletion of Aβ in the body itself (such as, e.g., in DeMattos et al., PNAS 98"-(5) (2001) 8850-8855 with peripheral anti-Aβ antibodies) and which are conducted over a longer period of time, the inventive combination therapy involves the decisive advantage that no autoimmune responses can be triggered. Furthermore, according to the invention no substances which can act only in the body (possibly only after having been transported to a specific site) have to be supplied to the patient, but the pathogenic agent is selectively removed, i.e. the cause of the disease is specifically removed in an extracorporeal manner, eliminating reaction products in the body not being necessary.

According to the invention, already existing and known apheresis devices in all embodiments can be easily adapted to the present invention. In particular, when choosing the solid carrier (and the apheresis device) its/their medical suitability should be taken into consideration. Such carriers, methods or devices are described i.a. in U.S. Pat. No. 5,476,715, U.S. Pat. No. 6,036,614, U.S. Pat. No. 5,817,528 or U.S. Pat. No. 6,551,266. Corresponding commercial apheresis apparatuses are i.a. distributed by Fresenius, Plasmaselect, ASAHI, Kaneka, Braun etc., offering, e.g., the systems LDL-Therasorb®, Immunosorba®, Prosorba®, Globafin®, Ig-Therasorb®, Immusorba®, Li-Posorba®, HELP®, DALI®, Bilirubin-Bile-Acid-Absorber BR-350, Promtheus® detoxication, MARS®, ADAsorb of Medicap or Plasma FLO. Although all these systems in their commercially available form are not always primarily directed on the specific elimination of a single protein, a person skilled in the art of apheresis can adapt them easily to the present invention, e.g. as immuno apheresis and/or by installing the inventive solid carrier (e.g. as column) into the apheresis device.

Therefore, according to the invention, by "APP-binding receptors" all substances are understood which have an affinity to the ligand APP and its biological by-products, in particular Aβ42, and which are capable of removing said polypeptides from the blood or plasma of AD patients or persons running the risk of getting AD. Said APP and Aβ42 receptors, respectively, preferably are (poly or monoclonal) antibodies, proteins, peptides, gangliosides or nucleic acids.

Anti-APP antibodies, anti-Aβ40 antibodies or anti-Aβ42 antibodies, APP-binding proteins, especially gelsolin, apoJ or apoE, APP-binding peptides, APP-binding gangliosides, especially GM1, or APP-binding nucleic acids, especially aptamers, or mixtures of said receptors, are particularly preferred.

Examples of such antibodies are 3D6 (Aβ1-5), 2H3 (Aβ1-12), 2G3 (Aβ33-40), 21F12 (Aβ33-42), 12H7 (Aβ33-42) (Johnson-Wood et al., PNAS 1977:1550-1555, 10D5, 16C11 (Bard et al., Nature Medicine 2000:916-919), the antibodies (m266, m243) described in DeMattos et al. (2001) as well as antibodies of same specificity. Such antibodies are obtained e.g., when immunizing mammals with vaccine formulations comprising APP, Aβ42 or fragments or variants thereof, optionally followed by cell fusion and clone selection protocols (with monoclonal antibodies).

Further examples for APP-binding protein receptors are gelsolin (Matsuoka et al. 2003, see above), apoJ and apoE (DeMattos et al., 2001, see above). GM1 is an example of an APP-binding ganglioside receptor (Matsuoka et al., 2003, see above).

In this contexts peptides serving as APP-binding receptors may be composed of D or L amino acids or combinations of D and L amino acids and may optionally be modified by further modifications, ring formations or derivatizations. Suitable peptide receptors for e.g., Aβ42, can be provided from commercially available peptide libraries. These peptides are preferably at least 5 preferably 6 amino acids in length, in particular at least 8 amino acids, wherein the preferred lengths may be up to 10, preferably up to 14 or 20 amino acids. According to the invention, however, also longer peptides can be used as APP-binding receptors without any problems. Moreover, oligomers (such as, e.g. polyethylenimine and polylysine) are suitable receptors.

Of course, phage libraries, peptide libraries (see above) or structure libraries, e.g. obtained by combinatorial chemistry or high-throughput screening techniques for different structures, are also suitable for producing such APP-binding receptors.

Furthermore, APP-binding receptors can be used which are based on nucleic acids ("aptamers"; but also "decoy" oligodeoxynucleotides (ds oligonucleotides that constitute binding sites for transcription factors in terms of their sequence)), wherein said nucleic acids can be detected by various (oligonucleotide) libraries (e.g. with 2-160 nucleic acid residues) (for example, Burgstaller et al., Curr. Opin. Drug Discov. Dev. 5 (5) (2002), 690-700; Famulok et al., Acc. Chem. Res. 33 (2000), 591-599, Mayer et al.; PNAS 98 (2001), 4961-4965; and many others). The backbone of the nucleic acid can be detected, e.g., natural phosphor diester compounds and also by phosphorothioate or combinations or chemical variations (e.g. as PNA), wherein according to the invention primarily U, T, A, C, G, H and mC can be used as bases. The 2' residues of the nucleotides, which can be used according to the present invention, preferably are H, OH or other protective groups and modifications at the 2' position, wherein the nucleic acids can also be modified e.g. provided with protective groups, as they are usually used in oligonucleotide synthesis. By "protective group" an etherization of the oxygen atom is understood, whereas the —OH-group is replaced by something different in the 2'-modification. Many different possibilities are described in the prior art for both versions; methyl, allyl propyl and the like protective groups (i.e., e.g., 2'-OCH$_3$, 2'-O—CH=CH$_3$, etc.) are particularly preferred; particularly preferred modifications are 2'-deoxy, 2'-amino, 2'-fluoro, 2'-bromo, 2'-azido but also metals, such as selenium, etc. Furthermore, according to the invention also oligonucleotide stabilizing methods, which have been developed for the antisense technology (ribozymes, RNAi etc.), may be used for providing nucleic acids (compare, e.g., the companies ISIS and Ribozyme Pharmaceuticals leading in this field, in particular their patent documents and homepages).

This is why APP-binding aptamers (which, according to the invention and as defined above, also include Aβ42-binding aptamers) are also preferred APP-binding receptors in the scope of the present invention.

Therefore, APP-binding receptors which preferably consist of peptides, antibodies or nucleic acids, are used as carrier material for extracorporeally eliminating APP and its proteolytic decomposition products in Alzheimer patients and those running the risk of getting Alzheimer.

When using the present invention in medicinal routine practice, the carrier is required to be sterile and pyrogen-free so that every carrier substance and every receptor/carrier combination, respectively, which meets these characteristics, is preferred according to the present invention (see, e.g., U.S. Pat. No. 6,030,614 or U.S. Pat. No. 5,476,715). Among the suitable examples are porous homopolymers, co- or terpolymers of monomers containing vinyl (e.g. acrylic acid such as, e.g. TSK Toyopearl, Fractogel TSK), carriers with modifications (activations) with compounds containing oxirane (e.g. epichlorohydrine) and optionally further reactions with compounds containing NH$_3$, amino or carboxyl, or CNBr or CNCL absorbents as described in EP 110,409 A and DE 36,17,672 A. Particularly preferred adsorption materials for therapeutic purposes are suitable for avoiding a loss of blood cells, do not or only little activate the complementing system and delay aggregate formation in the extracorporeal circulation as far as possible. Furthermore, the used carrier materials should preferably be sufficiently stable against sterilization measures also in receptor-coupled form, in particular against ethylene oxide saturation, glutaraldehyde saturation, gamma radiation, treatments with vapor, UV, solvents and/or detergents, etc. Products based on sepharose, agarose, acrylic, vinyl and dextran etc., may also be used, their preferably suitable functional groups for binding to the APP-binding receptors being already commercially available. Further suitable carriers also include monoliths (carriers based on cross-linked glycidylmethacrylate-co-ethyleneglycoldimethacrylate polymer).

Chemistry known to the person skilled in the art can be used for coupling the receptors to the appropriate carriers (e.g. Bioconjugate Techniques, Greg T Hermanson, Ed., Academic Press, Inc. San Diego, Calif., 1995, 785 pp).

According to a further aspect the present invention relates to the use of the inventive device for providing a treatment of or a treatment device for Alzheimer's Disease or for preventing such a disease in the scope of the inventive combination therapy, by adapting the device to be suitable for the treatment of the respective patient. When conducting the treatment, a patient is sufficiently long connected with the apheresis device for effectively eliminating APP polypeptides, wherein the blood or plasma flux of the patient is brought into contact with the solid carrier that comprises the APP-binding receptor, whereupon APP and/or the proteolytic decomposition products of APP, in particular Aβ42, are bound. In the course of the apheresis treatment, certainly, peripheral or central venous vein access and arteriovenous fistula are to be ensured, as well as sufficient anticoagulation, and the required quantification and measure data are to be recorded. Moreover, most of the apheresis methods require a primary separation of plasma and blood cells before the plasma treatment proper. Special persons who require such a prophylactic measure are persons with a familial factor older persons (>50, >60 or >70 years) or persons having another risk factor for AD, in particular genetic factors.

According to a further central aspect, the present invention relates to a method for preventing or treating Alzheimer's Disease (AD), wherein
    an agent for inducing a sequestration of amyloid β (Aβ) into plasma is administered to a person and the person is treated with an apheresis device that comprises a solid carrier which can be brought into contact with the blood or the plasma flux, said carrier having an amyloid-β-precursor-protein (APP)-binding receptor, wherein APP is removed from the blood of the person by means of the apheresis device.

Said method is preferably conducted with the inventive kit.

Accordingly, the present invention also relates to the use of Aβ mimotopes, as defined above, for producing an agent which is to be used in an inventive combination treatment for preventing or treating AD.

The invention will be explained in more detail by way of the following examples, to which it is, certainly, not restricted.

1. Production of the Carrier Carrying the App Receptor 1.1. Monolithic Column

A CIM® Epoxy Monolithic Column (BIA Separations, SI) is equilibrated with 0.5 M Na-phosphate buffer at an pH of 8.0 according to the producer's instruction and a monoclonal antibody against Aβ peptide is also activated according to the producer's instruction and is coupled to the CIM column. The column is washed several times with phosphate buffer (+1 M NaCl) and, optionally, the surplus epoxy groups are blocked.

Quality assurance is done by controlling the wash and equilibration eluate; only columns without active epoxy groups and without antibody leakage in the eluate are used in the further process and installed in an apheresis apparatus.

1.2 Sepharose Column

An agarose bulk material (sepharose CL4B) is aseptically filled into a sterile and pyrogen-free container and the material is aseptically washed, wherein the gel material is completely dried under vacuum between every washing step. The sepharose is then sterilized under vapor in the autoclave for 30 minutes at 115° C.

After sterilization, the sepharose is taken up in 60% acetone/water in a sterile container and is activated with CNBr and triethylamine (14 g CNBr per 96 ml actone; 30 ml triethylamine in C66.2 ml 87%-acetone). Then, an acetone/HCl solution was added (392 ml sterile, pyrogen-free water; 16.3 ml 5 N HCL, 408 ml acetone). The activated sepharose is washed and supplied to the coupling reaction within 2 h to prevent hydrolysis of activated groups.

A sterile-filtered antibody solution (m266 or m243, respectively) is introduced into the reaction vessel and stirred for at least 90 min. Finally, the reaction solution is thoroughly washed (with isotonic phosphate buffer) until no reaction products are detectable in the eluate, the antibody-coupled sepharose is filled into sterile and depyrogenized glass columns with glass sinters and a final quality assurance is conducted (eluate analysis with respect to reaction products, heavy metals, etch; particle analysis, pyrogenity; sterility).

2. Animal Model for Apheresis Treatment of Alzheimer Patients

In the last years a special extracorporeal system for experimental apheresis in freely movable small animals has been developed at the Institute of Diabetes "Gerhard Katsch" in Karlsburg, Germany. This apheresis therapy can be repeatedly conducted with one and the same animal. Moreover, the animals used can also be included in subsequent studies for long-term evaluation of the apheresis therapy. The use of said experimental apheresis system has been successfully demonstrated in several rat strains. Repeated apheresis treatment was well-tolerated by rats with Typ-1 diabetes and collogen typ II-induced arthritis when their body weight was more than 250 g.

Before the experimental apheresis therapy starts, the animals are provided with arterial and venous catheters. In a first step of the apheresis blood cells and plasma are separated by means of a plasma filter. While the blood cells are directly reinfused into the animal (via the venous catheter), the separated plasma is guided passed the adsorption agent produced in Example 1 (wherein the ligands are separated from the plasma due to the binding to the immobilized receptors), before it is resupplied to the animal.

Alternatively a whole-blood apheresis may also be conducted, e.g. analogous thereto, as is done with the DALI apheresis for LDL.

3. Inventive Combination Therapy in the Animal Model:

The combination therapy in the animal model can basically be conducted such that the Aβ efflux occurs before, during or after apheresis. Furthermore, the frequency of the application of the two therapies relative to each other can be varied.

---

The invention claimed is:

1. A method for treating Alzheimer's disease in a person, comprising:
administering to the person an agent for inducing an efflux of amyloid β (Aβ) from the brain to the plasma of the person, wherein said agent is an Aβ-mimotope comprising a peptide selected from the group consisting of EIDYHR (SEQ ID NO: 2), ELDYHR (SEQ ID NO: 3), EVDYHR (SEQ ID NO: 4), DIDYHR (SEQ ID NO: 5), DLDYHR (SEQ ID NO: 6), DVDYHR (SEQ ID NO: 7), DIDYRR (SEQ ID NO: 8), DLDYRR (SEQ ID NO: 9), DVDYRR (SEQ ID NO: 10), DKELRI (SEQ ID NO: 11), DWELRI (SEQ ID NO: 12), YREFFI (SEQ ID NO: 13), YREFRI (SEQ ID NO: 14), YAEFRG (SEQ ID NO: 15), EAEFRG (SEQ ID NO: 16), DYEFRG (SEQ ID NO: 17), ELEFRG (SEQ ID NO: 18), DRELRI (SEQ ID NO: 19), DKELKI (SEQ ID NO: 20), DRELKI (SEQ ID NO: 21), GREFRN (SEQ ID NO: 22), EYEFRG (SEQ ID NO: 23), DWEFRDA (SEQ ID NO: 24), SWEFRT (SEQ ID NO: 25), DKELR (SEQ ID NO: 26), SFEFRG (SEQ ID NO: 27), DAEFRWP (SEQ ID NO: 28), DNEFRSP (SEQ ID NO: 29), SAEFRTQ (SEQ ID NO: 32), SAEFRAT (SEQ ID NO: 33), SWEFRNP (SEQ ID NO: 34), SWEFRLY (SEQ ID NO: 35), SWELRQA (SEQ ID NO: 36), SVEFRYH (SEQ ID NO: 37), SYEFRHH (SEQ ID NO: 38), SQEFRTP (SEQ ID NO: 39), SSEFRVS (SEQ ID NO: 40), DWEFRD (SEQ ID NO: 41), DAELRY (SEQ ID NO: 42), DWELRQ (SEQ ID NO: 43), SLEFRF (SEQ ID NO: 44), GPEFRW (SEQ ID NO: 45), and GKEFRT (SEQ ID NO: 46); and
treating said person with an apheresis device to maintain the Aβ efflux, wherein said apheresis device comprises a solid carrier comprising an amyloid-β-precursor protein binding receptor (APP-binding receptor), wherein said APP-binding receptor is selected from the group consisting of gelsolin, an anti-Aβ antibody, an anti-APP antibody, apolipoprotein J (apoJ), apolipoprotein E (apoE), and GM1 ganglioside, and wherein said APP-binding receptor binds and removes Aβ from the plasma when said solid carrier of said apheresis device is brought into contact with the plasma of said person.

2. The method according to claim 1, wherein said agent and said apheresis device are obtained from a kit.

3. The method according to claim 1, wherein the peptide is not more than 15 amino acids in length.

4. The method according to claim 1, wherein the peptide is from 6 to 12 amino acids in length.

5. The method according to claim 1, wherein the peptide is from 9 to 11 amino acids in length.

6. The method according to claim 1, wherein the peptide is covalently or non-covalently coupled to a linker or carrier.

7. The method according to claim 2, wherein the peptide is covalently or non-covalently coupled to a linker or carrier.

8. The method according to claim 3, wherein the peptide is covalently or non-covalently coupled to a linker or carrier.

9. The method according to claim 4, wherein the peptide is covalently or non-covalently coupled to a linker or carrier.

10. The method according to claim 5, wherein the peptide is covalently or non-covalently coupled to a linker or carrier.

* * * * *

SEQUENCE LISTING

```
<160> NUMBER OF SEQ ID NOS: 51

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct

<400> SEQUENCE: 1

Asp Ala Glu Phe Arg His
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct

<400> SEQUENCE: 2

Glu Ile Asp Tyr His Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Glu Leu Asp Tyr His Arg
1               5
```

```
<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Glu Val Asp Tyr His Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Asp Ile Asp Tyr His Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct

<400> SEQUENCE: 6

Asp Leu Asp Tyr His Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

Asp Val Asp Tyr His Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Asp Ile Asp Tyr Arg Arg
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Asp Leu Asp Tyr Arg Arg
1               5
```

```
<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Asp Val Asp Tyr Arg Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Asp Lys Glu Leu Arg Ile
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Asp Trp Glu Leu Arg Ile
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

Tyr Arg Glu Phe Phe Ile
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Tyr Arg Glu Phe Arg Ile
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Construct

<400> SEQUENCE: 15

Tyr Ala Glu Phe Arg Gly
1               5
```

```
<210> SEQ ID NO 16
<211> LENGTH: 6
<212> TYPE: PRT
<213> ORGANISM: Artificial Sequence
<220> FEATURE:
<223> OTHER INFORMATION: Synthetic Construct

<400> SEQUENCE: 16

Glu Ala Glu Phe Arg Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Asp Tyr Glu Phe Arg Gly
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Glu Leu Glu Phe Arg Gly
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19

Asp Arg Glu Leu Arg Ile
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Asp Lys Glu Leu Lys Ile
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Asp Arg Glu Leu Lys Ile
1               5
```

```
<210> SEQ ID NO 22
<211> LENGTH: 6
<212> TYPE: PRT
<213> ORGANISM: Artificial Sequence
<220> FEATURE:
<223> OTHER INFORMATION: Synthetic Construct

<400> SEQUENCE: 22

Gly Arg Glu Phe Arg Asn
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

Glu Tyr Glu Phe Arg Gly
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic Construct

<400> SEQUENCE: 24

Asp Trp Glu Phe Arg Asp Ala
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Construct

<400> SEQUENCE: 25

Ser Trp Glu Phe Arg Thr
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Asp Lys Glu Leu Arg
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Ser Phe Glu Phe Arg Gly
1               5
```

```
<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Asp Ala Glu Phe Arg Trp Pro
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Asp Asn Glu Phe Arg Ser Pro
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Gly Ser Glu Phe Arg Asp Tyr
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Gly Ala Glu Phe Arg Phe Thr
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Ser Ala Glu Phe Arg Thr Gln
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic Construct

<400> SEQUENCE: 33

Ser Ala Glu Phe Arg Ala Thr
1               5
```

```
<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Ser Trp Glu Phe Arg Asn Pro
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Ser Trp Glu Phe Arg Leu Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Ser Trp Glu Leu Arg Gln Ala
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic Construct

<400> SEQUENCE: 37

Ser Val Glu Phe Arg Tyr His
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38

Ser Tyr Glu Phe Arg His His
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

Ser Gln Glu Phe Arg Thr Pro
1               5
```

```
<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

Ser Ser Glu Phe Arg Val Ser
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Construct

<400> SEQUENCE: 41

Asp Trp Glu Phe Arg Asp
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic Construct

<400> SEQUENCE: 42

Asp Ala Glu Leu Arg Tyr
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic Construct

<400> SEQUENCE: 43

Asp Trp Glu Leu Arg Gln
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Construct

<400> SEQUENCE: 44

Ser Leu Glu Phe Arg Phe
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct

<400> SEQUENCE: 45

Gly Pro Glu Phe Arg Trp
1               5
```

-continued

```
<210> SEQ ID NO 46
<211> LENGTH: 6
<212> TYPE: PRT
<213> ORGANISM: Artificial Sequence
<220> FEATURE:
<223> OTHER INFORMATION: Synthetic Construct

<400> SEQUENCE: 46

Gly Lys Glu Phe Arg Thr
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic Construct

<400> SEQUENCE: 47

Ala Tyr Glu Phe Arg His
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Nle

<400> SEQUENCE: 48

Asp Lys Glu Xaa Arg
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Nva

<400> SEQUENCE: 49

Asp Lys Glu Xaa Arg
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Cha

<400> SEQUENCE: 50

Asp Lys Glu Xaa Arg
1               5
```

```
<210> SEQ ID NO 51
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: wherein Xaa at positions 1 to 6 is an amino
      acid other than cysteine, with the proviso that the peptide
      defined by Xaa at positions 1 to 6 is a peptide other than
      DAEFRH

<400> SEQUENCE: 51

Xaa Xaa Xaa Xaa Xaa Xaa
1               5
```